US008634902B2

(12) United States Patent
Benser et al.

(10) Patent No.: US 8,634,902 B2
(45) Date of Patent: Jan. 21, 2014

(54) CARDIAC ANALYSIS SYSTEM FOR COMPARING CLINICAL AND INDUCED VENTRICULAR TACHYCARDIA EVENTS

(75) Inventors: Michael E. Benser, Valencia, CA (US); Gene A. Bornzin, Simi Valley, CA (US); Euljoon Park, Valencia, CA (US); Kyungmoo Ryu, Palmdale, CA (US); Michael Hardage, Kingwood, TX (US)

(73) Assignee: Pacesetter, Inc., Sylmar, CA (US)

( * ) Notice: Subject to any disclaimer, the term of this patent is extended or adjusted under 35 U.S.C. 154(b) by 832 days.

(21) Appl. No.: 12/820,879

(22) Filed: Jun. 22, 2010

(65) Prior Publication Data

US 2011/0282226 A1 Nov. 17, 2011

Related U.S. Application Data

(60) Provisional application No. 61/333,617, filed on May 11, 2010.

(51) Int. Cl.
*A61B 5/04* (2006.01)

(52) U.S. Cl.
USPC .......................................................... 600/510

(58) Field of Classification Search
USPC ................................................. 600/508–523
See application file for complete search history.

(56) References Cited

U.S. PATENT DOCUMENTS

| | | | |
|---|---|---|---|
| 5,421,830 A | 6/1995 | Epstein et al. | |
| 5,509,927 A | 4/1996 | Epstein et al. | |
| 6,438,407 B1 | 8/2002 | Ousdigian et al. | |
| 2004/0172067 A1* | 9/2004 | Saba | 607/4 |
| 2008/0125824 A1 | 5/2008 | Sauer et al. | |

FOREIGN PATENT DOCUMENTS

| | | |
|---|---|---|
| WO | 0170331 A2 | 9/2001 |
| WO | 0170331 A3 | 3/2002 |
| WO | 0170331 A3 | 4/2002 |

* cited by examiner

*Primary Examiner* — Carl H Layno
*Assistant Examiner* — Paula J Stice

(57) ABSTRACT

A cardiac analysis system is provided that includes an implantable medical device (IMD), at least one sensor, and an external device. The IMD has electrodes positioned proximate to a heart that sense first cardiac signals of the heart and associated with a clinical ventricular tachycardia (VT) event and second cardiac signals associated with an induced VT event. The sensor measures first and second cardiac parameters of the heart associated with the clinical and induced VT events, respectively. The external device is configured to receive the first and second cardiac signals associated with the clinical and the induced VT events and the first and second cardiac parameters associated with the clinical and the induced VT events. The external device compares the first and second cardiac signals and compares the first and second cardiac parameters to determine if the clinical and induced VT events are a common type of VT event.

18 Claims, 7 Drawing Sheets

136 138 140 142
114 112 106
116 102
EXTERNAL DEVICE
EVALUATION PROCESSOR
100
110 108
DISPLAY DEVICE
144
124
126 128 134
132
150
148
146
130
122
120
118
104

VL TIP
AL RING
AL COIL
AR TIP
CASE
VR RING
VR TIP
RV COIL
SVC COIL
ELECT. CONFIG. SWITCH 524
ATRIAL PULSE GENERATOR
ATR. SENSE
VTR. SENSE
VENTR. PULSE GENERATOR
SHOCKING CIRCUIT
A/D
PROGRAMMABLE MICRO-CONTROLLER 516
PACING MODULE
COMPARISON MODULE
MEMORY
TELEMETRY CIRCUIT
PHYSIOLOGIC SENSOR
IMPEDANCE MEASURING CIRCUIT
EXTERNAL DEVICE

CARDIAC ANALYSIS SYSTEM FOR COMPARING CLINICAL AND INDUCED VENTRICULAR TACHYCARDIA EVENTS

CROSS REFERENCE TO RELATED APPLICATIONS

This application claims the benefit of U.S. Provisional Application Ser. No. 61/333,617, filed May 11, 2010.

FIELD OF THE INVENTION

Embodiments of the presently describe subject matter generally pertain to implantable medical devices and more particularly to methods and systems that compare clinical ventricular tachycardia (VT) events with induced VT events to determine if the clinical and induced VT events are similar.

BACKGROUND OF THE INVENTION

An implantable medical device (IMD) is implanted in a patient to monitor, among other things, electrical activity of a heart and to deliver appropriate electrical therapy, as required. IMDs include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. IMDs sense cardiac signals of the heart to determine if and when to apply stimulus pulses.

Ventricular tachycardia (VT) is a cardiac event where the ventricles of the heart contract at an advanced rate. VT events begin in one or both ventricles of the heart. VT events are life-threatening arrhythmias that may develop into ventricular fibrillation, asystole, or sudden death. Ablation procedures may be applied to the heart to treat VT. For example, areas of the myocardium may be exposed to radiofrequency energy that is delivered to the myocardium through a percutaneous catheter. During ablation, the radiofrequency energy is applied to the strategic or predetermined locations along the ventricular myocardium. Ablation may prevent future VT events or reduce the frequency of future VT events.

During an ablation procedure, the physician must first determine the area to ablate. To identify the area to ablate, the physician induces a VT event. The physician attempts to induce a VT event that is similar to previous clinical VT events of the patient and then ablate the sections of the ventricular myocardium that manifest or sustain the induced VT events. The ablated myocardium will not be able to manifest or sustain future clinical VT events. A clinical VT event represents a VT event that occurs outside of a medical facility, or a VT event that occurs without any provocative maneuver, such as a VT event that is not induced by delivering stimulus pulses to the heart.

However, existing ablation procedures have certain limitations. In the electrophysiology (EP) lab where the ablation procedure is performed, the induced VT event may not be similar to the clinical VT event. For example, the induced VT event may have different rotor pathways and/or focal trigger locations when compared to previous clinical VT events. The physician may not know if the induced VT event is the same as or similar to the previous clinical VT events. If the induced VT event is dissimilar from the previous clinical VT events, then the induced VT event may lead to identification of a non-clinically relevant area to ablate. The non-clinically relevant area may not be involved with previous clinical VT events. Hence, the ablation procedure may not be successful in preventing future clinical VT events.

A need exists for methods and systems that provide physicians who apply ablation procedures with additional information that indicates whether an induced VT event is the same as or similar to previous clinical VT events. Such information may be useful in ensuring that an ablation procedure is applied to the correct regions of the heart to prevent future clinical VT events.

BRIEF SUMMARY OF THE INVENTION

In one embodiment, a cardiac analysis system is provided. The system includes an implantable medical device (IMD), at least one sensor, and an external device. The IMD comprises electrodes positioned proximate to a heart that sense first cardiac signals of the heart associated with a clinical ventricular tachycardia (VT) event of the heart and sense second cardiac signals associated with an induced VT event of the heart. The at least one sensor measures first cardiac parameters of the heart associated with the clinical VT event and measures second cardiac parameters associated with the induced VT event. The external device receives the first cardiac signals associated with the clinical VT event and receives the second cardiac signals associated with the induced VT events. The external device also receives the first cardiac parameters associated with the clinical VT event and the second cardiac parameters associated with the induced VT event. The external device compares the second cardiac signals associated with the induced VT event with the first cardiac signals associated with the clinical VT event and compares the second cardiac parameters associated with the induced VT event with the first cardiac parameters associated with the clinical VT event to determine when the clinical and induced VT events are a common type of VT event.

In another embodiment, a method for comparing ventricular tachycardia (VT) events of a heart is provided. The method includes sensing cardiac signals of the heart using electrodes positioned proximate to the heart. The cardiac signals include first cardiac signals associated with a clinical VT event and second cardiac signals associated with an induced VT event. The method also includes measuring cardiac parameters representative of the heart using at least one sensor. The cardiac parameters include first cardiac parameters associated with the clinical VT event and second cardiac parameters associated with the induced VT event. The method includes comparing the first cardiac signals associated with the clinical VT event with the second cardiac signals associated with the induced VT event and comparing the first cardiac parameters associated with the clinical VT event with the second cardiac parameters associated with the induced VT event to determine when the clinical VT event and the induced VT event are a common type of VT event.

In another embodiment, a tangible and non-transitory computer readable storage medium for a cardiac analysis system comprising an implantable medical device (IMD) having electrodes positioned proximate to a heart, at least one sensor, and an evaluation processor is provided. The computer readable storage medium includes instructions to direct the evaluation processor to receive cardiac signals sensed by the electrodes of the IMD and receive cardiac parameters measured by the at least one sensor. The cardiac signals and the cardiac parameters are representative of cardiac activity of the heart. The cardiac signals include first cardiac signals associated with a clinical ventricular tachycardia (VT) event and the cardiac parameters include first cardiac parameters associated with the clinical VT event. The instructions also direct the evaluation processor to receive second cardiac signals associated with an induced VT event and to receive second cardiac parameters associated with the induced VT event. The instructions direct the evaluation processor to determine when the clinical VT event and the induced VT event are a common type of VT event by comparing the first cardiac signals associated with the clinical VT event with the second cardiac signals associated with the induced VT event and comparing the first cardiac parameters associated with the clinical VT event with the second cardiac parameters associated with the induced VT event.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the presently described subject matter may be practiced. These embodiments, which are also referred to herein as "examples," are described in sufficient detail to enable those skilled in the art to practice the disclosed subject matter. It is to be understood that the embodiments may be combined or that other embodiments may be utilized, and that structural, logical, and electrical variations may be made without departing from the scope of the presently described subject matter. The following detailed description is, therefore, not to be taken in a limiting sense, and the scope of the presently described subject matter is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
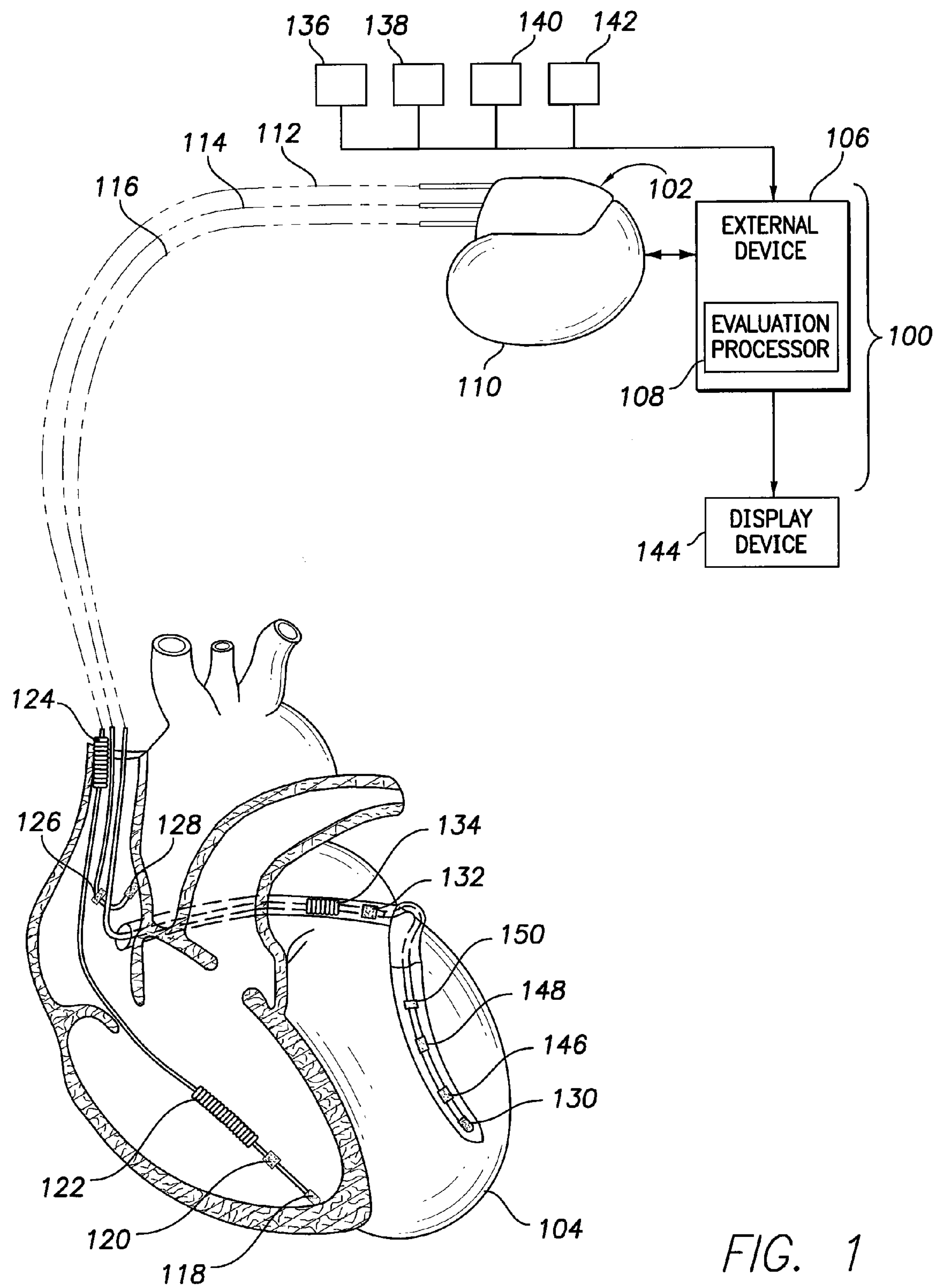
FIG. 1 illustrates a cardiac analysis system in accordance with one embodiment.

FIG. 1 illustrates a cardiac analysis system 100 in accordance with one embodiment. The system 100 includes an implantable medical device (IMD) 102 that is coupled to a heart 104. The system 100 also includes an external device 106 having an evaluation processor 108 that is communicatively coupled with the IMD 102. The IMD 102 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like. The IMD 102 includes a housing 110 that is joined to several leads 112, 114, 116. The leads 112, 114, 116 are located at various locations of the heart 104, such as an atrium, a ventricle, or both, to measure cardiac signals of the heart 104. The leads 112, 114, 116 include the right ventricular (RV) lead 112, the right atrial (RA) lead 114, and the coronary sinus lead 116.

Several electrodes 118, 120, 122, 124, 126, 128, 130, 132, 134, 146, 148, 150 are coupled with the leads 112, 114, 116 for sensing cardiac signals and/or for delivering stimulus or stimulation pulses to the heart 104. The housing 110 may be one of the electrodes and is often referred to as the "can", "case", or "case electrode." The electrodes 118, 120, 122, 124, 126, 128, 130, 132, 134, 146, 148, 150 include an RV tip electrode 118, an RV ring electrode 120, an RV coil electrode 122, a superior vena cava (SVC) electrode 124, a right atrial (RA) ring electrode 126, an RA tip electrode 128, a left ventricular (LV) tip electrode 130, a left atrial (LA) ring electrode 132, an LA coil electrode 134, and intermediate LV electrodes 146, 148, 150. Leads and electrodes other than those shown in FIG. 1 may be included in the IMD 102 and positioned in or proximate to the heart 104. Not all of the electrodes 118, 120, 122, 124, 126, 128, 130, 132, 134, 146, 148, 150 may be necessary to perform all embodiments described herein. For example, subsets of the electrodes 118, 120, 122, 124, 126, 128, 130, 132, 134, 146, 148, 150 may be used in connection with one or more different embodiments.

The IMD 102 monitors cardiac signals of the heart 104 and communicates the cardiac signals to the external device 106. The external device 106 may be a computerized diagnostic system or device that includes the evaluation processor 108 to examine, among other things, cardiac signals of the heart 104. For example, the external device 106 may be a computer that includes a microprocessor operating based on software or other instructions stored on a tangible and non-transitory computer readable storage medium, such as a ROM, RAM, or hard drive memory 604, 606, 608 (shown in FIG. 6). The evaluation processor 108 may be the microprocessor of the external device 106 or another logic based device that operates based on the software or instructions stored on the ROM, RAM, or hard drive memory 604, 606, 608.

The IMD 102 senses cardiac signals during and/or following different ventricular tachycardia (VT) events of the heart 104. In one embodiment, a VT event occurs when the heart rate increases to at least 100 beats per minute. The IMD 102 senses the cardiac signals during and/or following a clinical VT event of the heart 104 and cardiac signals during and/or following an induced VT event of the heart 104. The clinical VT event is an episode of VT that is not induced or caused by delivery of stimulus pulses to the heart 104 by the IMD 102. The clinical VT events may be VT episodes that occur outside of a medical setting, such as outside of a physician's office, hospital, clinic, or laboratory, such as an electrophysiology (EP) lab, or a VT event that occurs without any provocative maneuver. The induced VT event is an episode of VT that is caused by application of stimulus pulses to the heart 104 by the IMD 102. The induced VT events may be VT episodes that are induced in a medical setting to provide treatment or a procedure to the heart 104. The clinical VT event may occur prior to the patient being admitted to an EP lab to receive an ablation procedure to the patient's heart 104 while the induced VT event may occur when the patient in is an EP lab receiving an ablation procedure to the heart 104.

In one embodiment, the IMD 102 measures cardiac indices based on the cardiac signals during and/or following the clinical and induced VT events. A cardiac index represents a measurement of activity of the heart 104 using one or more of the electrodes 118, 120, 122, 124, 126, 128, 130, 134, 146, 148, 150 that are positioned proximate to the heart 104. For example, the electrodes 118, 120, 122, 124, 126, 128, 130, 134, 146, 148, 150 may be positioned within and/or outside of the heart 104. Alternatively, a cardiac index may be a calculation that represents activity of the heart 104 and is based on cardiac signals sensed by the electrodes 118, 120, 122, 124, 126, 128, 130, 134, 136, 146, 148, 150. The cardiac indices may be measured using the electrodes 118, 120, 122, 124, 126, 128, 130, 132, 134, 146, 148, 150. Several examples of cardiac indices are described below and include, without limitation, various characteristics and morphologies of cardiac signal waveforms, cardiogenic impedance vectors, and left atrial pressure (LAP) measurements. Cardiogenic impedance vectors represent electrical impedance characteristics of vectors measured between predetermined combinations of the electrodes 118, 120, 122, 124, 126, 128, 130, 132, 134, 146, 148, 150 and/or housing 110. For example, a cardiogenic impedance vector may be measured between the RV coil electrode 122 and the housing 110, between the RV tip electrode 118 and the housing 110, between the SVC coil electrode 124 and the housing 110, or between two electrodes 118, 120, 122, 124, 126, 128, 130, 132, 134, 146, 148, 150 positioned within the heart 104.

In the illustrated embodiment, several sensors 136, 138, 140, 142 are communicatively coupled with the external device 106. While four sensors 136, 138, 140, 142 are shown, alternatively a different number of sensors may be provided. The sensors 136, 138, 140, 142 may be located outside and/or inside of the heart 104 and monitor various cardiac parameters of the heart 104. A cardiac parameter is a physiologic measurement of activity of the heart 104 that is obtained by one or more of the sensors 136, 138, 140, 142. Examples of cardiac parameters include, but are not limited to, blood pressure measurements, measurements of the oxygen content in a patient's blood, a volume of the heart 104, acoustic noise of the heart 104, and the like. The sensors 136, 138, 140, 142 may be fairly complex or simple. For example, one or more of the sensors 136, 138, 140, 142 may monitor the voltages of electronic potentials as a cardiac parameter.

The sensors 136, 138, 140, 142 may be referred to as external sensors. Alternatively, the sensors 136, 138, 140, 142 may be positioned in the heart 104 and be referred to as internal sensors. The sensors 136, 138, 140, 142 may sense cardiac parameters that are representative of cardiac activity of the heart 104. The cardiac parameters may be uncorrelated to the cardiac signals sensed by the IMD 102. For example, the sensors 136, 138, 140, 142 may measure one or more cardiac parameters that are independent of, or are not directly proportional or related to, the cardiac signals, or that do not change based on a change in the cardiac signals. Alternatively, the sensors 136, 138, 140, 142 may measure one or more cardiac parameters that are correlated with the cardiac signals.

The sensors 136, 138, 140, 142 may be separate from the IMD 102 or incorporated into the IMD. For example, one or more sensors 136, 138, 140, 142 may be located on or otherwise incorporated with the housing 110 of the IMD, located on or otherwise incorporated with a lead of the IMD, or separate and spaced apart from the IMD 102. By way of non-limiting example only, the sensors 136, 138, 140, 142 may include a blood pressure sensor 136, a blood oxygen sensor 138, a photoplethysmograph (PPG) sensor 140, and external electrocardiograph (ECG) sensors 142. Other examples of sensors that may be used as one or more of the sensors 136, 138, 140, 142 include a glucose sensor that measures an amount of glucose in a patient's blood, a sensor that measures natriuretic peptide levels and/or catecholamine levels in the blood stream, an acoustic sensor that detects sounds of the heart 104, a saturated venous oxygen ($SvO_2$) sensor, and the like. During the clinical and induced VT events, the blood pressure sensor 136 may monitor the patient's blood pressure, the blood oxygen sensor 138 may measure the oxygen content of the patient, the PPG sensor 140 may measure the volume of the patient's heart 104, and/or the ECG sensors 142 may obtain far field cardiac signals of the heart 104. The sensors 136, 138, 140, 142 monitor the cardiac parameters and report the cardiac parameters to the external device 106. Alternatively, one or more of the sensors 136, 138, 140, 142 may communicate the cardiac parameters to the IMD 102. For example, one or more of the sensors 136, 138, 140, 142 may be communicatively coupled with the IMD 102 by a wireless connection.

The cardiac signals obtained by the IMD 102 during the clinical VT event and/or the induced VT event may be stored in an internal memory 528 (shown in FIG. 5) of the IMD 102 prior to communicating the cardiac signals to the external device 106. The cardiac parameters measured by the sensors 136, 138, 140, and/or 142 may be communicated to the external device 106 during and/or following the clinical and induced VT events.

The cardiac signals and cardiac parameters that are sensed during and/or following the clinical and induced VT events are communicated to the external device 106. In one embodiment, the cardiac signals and parameters obtained during and/or following the induced VT event are transmitted to the external device 106 as the cardiac signals and cardiac parameters are obtained. For example, the cardiac signals and cardiac parameters may be communicated to the external device 106 in real time. Real time communication of the cardiac signals and/or cardiac parameters may involve transmitting the cardiac signals and/or cardiac parameters as the signals and/or parameters are measured without introducing an intentional delay between measuring and communicating the cardiac signals and/or cardiac parameters. Alternatively, the IMD 102 may communicate the cardiac signals and cardiac parameters when one or more of the cardiac signals or cardiac parameters meet a predetermined criterion. For example, the IMD 102 may withhold transmission of the cardiac signals and cardiac parameters until a cardiac rate, such as a rate of ventricular contraction, exceeds a predetermined threshold.

The external device 106 may wirelessly receive the cardiac signals and cardiac parameters during application of an ablation procedure to the heart 104. The external device 106 communicates the cardiac signals and cardiac parameters to the evaluation processor 108. In one embodiment, the evaluation processor 108 presents the cardiac signals and the cardiac parameters so that an operator, clinician, or physician to evaluate and compare the cardiac signals and cardiac parameters. For example, the external device 106 may cause the cardiac signals and the cardiac parameters to be visually presented on the display device 144 so that a physician can compare the cardiac signals of the clinical VT event with the cardiac signals of the induced VT event, and compare the cardiac parameters of the clinical VT event with the cardiac parameters of the induced VT event. The physician may compare the cardiac signals and the cardiac parameters to determine if the clinical and induced VT events are a common type of VT event. Alternatively, the evaluation processor 108 may compare the cardiac parameters and cardiac signals of the clinical VT event with cardiac parameters and cardiac signals of the induced VT event to determine if the clinical and induced VT events are a common type of VT event.

The induced and clinical VT events may be a common type of VT event if the cardiac signals and/or cardiac parameters of the induced VT event are similar to the cardiac signals and/or cardiac parameters of the clinical VT event. A VT event begins at one or more focal triggers in the heart 104. A focal trigger is a location in the heart 104 where the VT event begins. For example, electric signals transmitted through the myocardium of the heart 104 may cause a VT event. The location where the electric signals begin is the focal trigger of the VT event. A rotor pathway is the area of the myocardium around which the electric signals are conducted during the VT event. Different VT events may have different focal triggers and/or rotor pathways. For example, a clinical VT event may have a focal trigger that is spaced apart from the focal trigger of an induced VT event if the clinical VT event and the induced VT event are not a common type of VT event. The rotor pathways through which the electric signals are conducted during the clinical VT event may differ from the rotor pathways of the induced VT event if the clinical VT event and the induced VT event are not a common type of VT event. Conversely, the focal triggers and/or rotor pathways of the clinical VT event and the induced VT event may be the same if the clinical VT event and the induced VT event are a common type of VT event.

Cardiac signals that are sensed by the electrodes 118, 120, 122, 124, 126, 128, 130, 132, 134, 146, 148, 150 during and/or following a VT event may be based on the electric signals conducted through the heart 104 during and/or following the VT event. For example, the cardiac signals sensed by the electrodes 118, 120, 122, 124, 126, 128, 130, 132, 134, 146, 148, 150 are affected by the electric signals of the clinical VT event and the induced VT event. The cardiac signals that are sensed by different electrodes 118, 120, 122, 124, 126, 128, 130, 132, 134, 146, 148, 150 may be affected differently. For example, if the focal trigger of a VT event is closer to the electrode 146 than the electrode 150, then the cardiac signals sensed by the electrode 146 may be impacted or altered more than the cardiac signals sensed by the electrode 150. In another example, if a rotor pathway of a VT event extends closer to the electrode 118 than the electrode 120, then the cardiac signals sensed by the electrode 118 may be impacted or altered more than the cardiac signals sensed by the electrode 120.

The cardiac signals sensed by the electrodes 118, 120, 122, 124, 126, 128, 130, 132, 134, 146, 148, 150 during and/or following the clinical VT event may be compared with the cardiac signals sensed by the electrodes during and/or following the induced VT event to determine if the clinical VT event and the induced VT event are a common type of VT event. The focal triggers and rotor pathways of the clinical VT event and the induced VT event create particular morphologies in the cardiac signals sensed by one or more of the electrodes 118, 120, 122, 124, 126, 128, 130, 132, 134, 146, 148, 150. Comparing the morphologies of the cardiac signals sensed by one or more of the electrodes 118, 120, 122, 124, 126, 128, 130, 132, 134, 146, 148, 150 during and/or following the induced VT event with the cardiac signals sensed by the same electrodes during and/or following the clinical VT event may reveal if the clinical VT event and the induced VT event are a common type of VT event.

The cardiac parameters measured by the sensors 136, 138, 140, 142 during and/or following the induced VT event may be compared with cardiac parameters measured by the sensors 136, 138, 140, 142 during and/or following the clinical VT event to determine or confirm that the induced VT event and the clinical VT event are a common type of event. For example, a patient's blood pressure may be similar during and/or following the clinical VT event and the induced VT event if the induced VT event is similar to the clinical VT event. In another example, the heart 104 may generate similar acoustic sounds if the clinical VT event and the induced VT event are a common type of VT event. The volume of the heart 104 may be approximately the same during and/or following the clinical VT event and the induced VT event if the clinical VT event and induced VT events are a common type of VT event.

The evaluation processor 108 compares cardiac signals obtained during and/or following the clinical VT event with cardiac signals obtained during and/or following the induced VT event and compares cardiac parameters measured during and/or following the clinical VT event with cardiac parameters measured during and/or following the induced VT event in order to determine if the clinical VT event and the induced VT event are a common type of VT event. For example, if differences between the cardiac signals of the clinical VT event and the cardiac signals of the induced VT event do not exceed one or more predetermined thresholds and differences between the cardiac parameters of the clinical VT event and the cardiac parameters of the induced VT event do not exceed one or more predetermined thresholds, then the induced VT event and the clinical VT event may be a common type of VT event. Conversely, if differences between the cardiac signals of the clinical VT event and the cardiac signals of the induced VT event exceed one or more predetermined thresholds and/or differences between the cardiac parameters of the clinical VT event and the cardiac parameters of the induced VT event exceed one or more predetermined thresholds, then the induced VT event and the clinical VT event may not be a common type of VT event.

The evaluation processor 108 determines if the clinical and induced VT events are similar so that an ablation procedure applied to the areas of the heart 104 based on the induced VT event also stops or prevents future clinical VT events. For example, if the ablation procedure is applied to locations of the heart 104 that stops the induced VT event during the ablation procedure, then future similar clinical VT events may be prevented from occurring.

Figure 2:
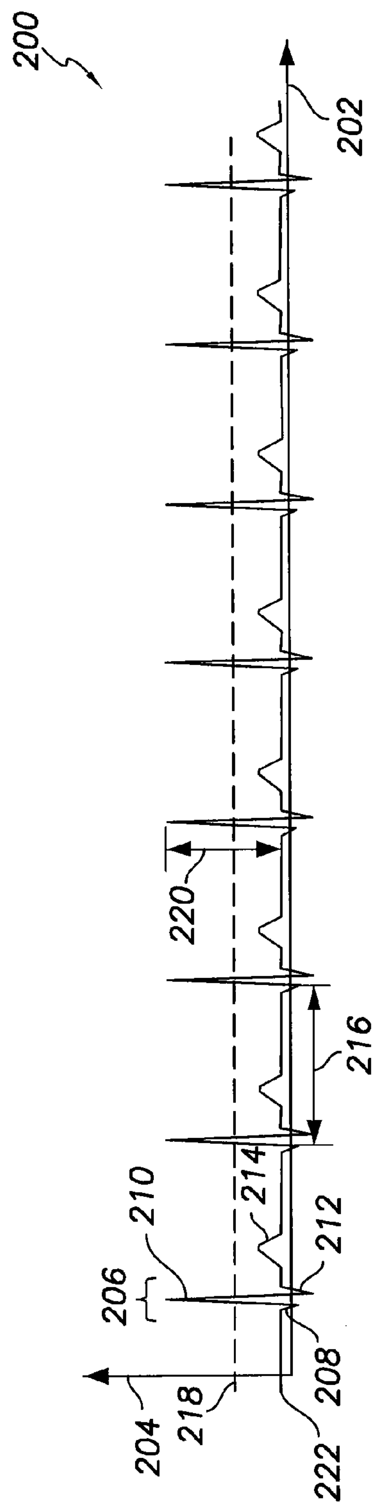
FIG. 2 illustrates ventricular waveforms of cardiac signals obtained by an implantable medical device shown in FIG. 1 during a clinical VT event in accordance with one embodiment.
Figure 3:
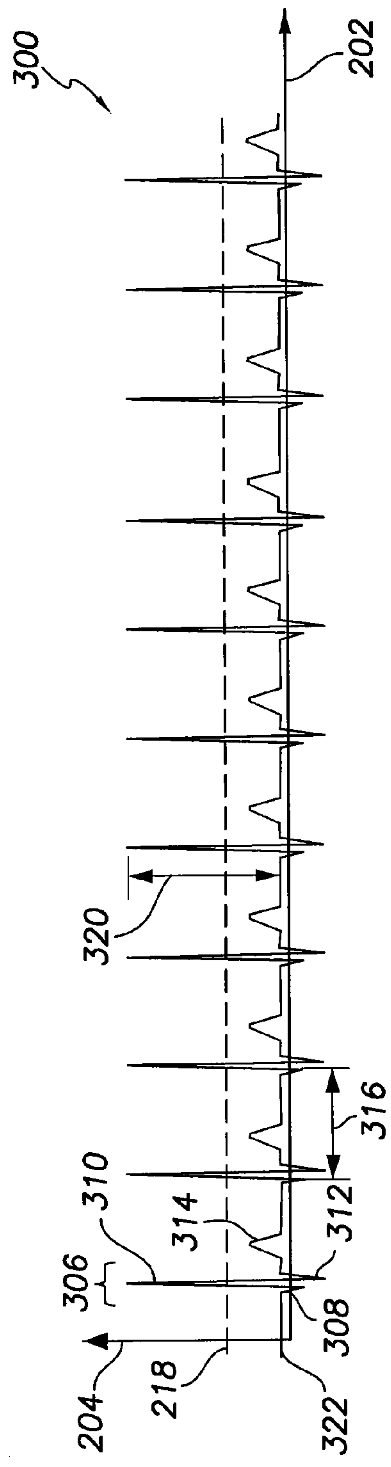
FIG. 3 illustrates ventricular waveforms of cardiac signals obtained by the implantable medical device of FIG. 1 during an induced VT event in accordance with one embodiment.

FIG. 2 illustrates ventricular waveforms 200 of the cardiac signals obtained by the IMD 102 (shown in FIG. 1) during and/or following a clinical VT event in accordance with one embodiment. FIG. 3 illustrates ventricular waveforms 300 of the cardiac signals obtained by the IMD 102 during and/or following an induced VT event in accordance with one embodiment. The ventricular waveforms 200, 300 are shown alongside a horizontal axis 202 representative of time and a vertical axis 204 representative of an amplitude or magnitude of the ventricular waveforms 200, 300. The ventricular waveforms 200, 300 are measured by the IMD 102 using one or more electrodes 118, 120, 122, 130, 146, 148, 150 (shown in FIG. 1) positioned within a ventricle of the heart 104 (shown in FIG. 1). These electrodes 118, 120, 122, 130, 146, 148, 150 may be referred to as ventricular electrodes. The ventricular waveforms 200, 300 include T-waves 214, 314 and QRS complexes 206, 306, which are comprised of Q-waves 208, 308, R-waves 210, 310, and S-waves 212, 312.

The evaluation processor 108 (shown in FIG. 1) may compare one or more cardiac indices of the ventricular waveforms 200, 300 to determine if the induced and clinical VT events are a common type of event. One cardiac index may be a VT cycle length 216, 316. The VT cycle length 216, 316 represents a time period of a ventricular cardiac cycle. The VT cycle lengths 216, 316 may be measured between common waveform segments of the ventricular waveforms 200, 300. For example, the VT cycle lengths 216, 316 may be measured as the time period between consecutive R-waves 210, 310 in the respective ventricular waveforms 200, 300. Alternatively, the VT cycle lengths 216, 316 may be measured between other waveform segments and/or non-consecutive waveforms segments. In the illustrated embodiment, the VT cycle lengths 216, 316 are measured as time periods between the ventricular waveforms 200, 300 exceeding a predetermined threshold 218. As shown in FIGS. 2 and 3, the R-waves 210, 310 exceed the threshold 218 and may be used to calculate the VT cycle lengths 216, 316.

The evaluation processor 108 (shown in FIG. 1) may compare variability indices of the VT cycle lengths 216, 316 to determine if the clinical and induced VT events are a common type of VT event. Each of the VT cycle lengths 216, 316 may vary with respect to time. For example, the VT cycle length 216 may not be constant during and/or following the clinical VT event as the IMD 102 (shown in FIG. 1) senses the cardiac signals of the ventricular waveforms 200. Similarly, the VT cycle length 316 may vary during and/or following the induced VT event. The variability indices of the VT cycle lengths 216, 316 represent the degrees to which the VT cycle lengths 216, 316 vary. In one embodiment, the variability indices may be calculated as standard deviations of the VT cycle lengths 216, 316 over the respective clinical and induced VT events. Alternatively, the variability indices may be calculated as other statistical measures of the amount of variance or change in the VT cycle lengths 216, 316.

The evaluation processor 108 (shown in FIG. 1) may compare a rate of ventricular contractions to determine if the clinical and induced VT events are a common type of event. The rates of ventricular contraction may be measured as a frequency at which a waveform segment, such as the QRS complexes 206, 306, occur in the ventricular waveforms 200, 300. The rates of the ventricular waveforms 200, 300 may be determined by measuring how frequently the ventricular waveforms 200, 300 exceed a predetermined threshold, such as the threshold 218. For example, the more frequently that the ventricular waveforms 200, 300 exceed the threshold 218, the larger the rate of ventricular contractions may be.

The evaluation processor 108 (shown in FIG. 1) may compare variability indices of the ventricular contractions to determine if the clinical and induced VT events are a common type of event. The rate variability indices of the ventricular waveforms 200, 300 represent variances in the rates of the ventricular waveforms 200, 300 vary. In one embodiment, the rate variability indices may be calculated as standard deviations of the rates of the ventricular waveforms 200, 300 during and/or following the respective clinical and induced VT events. Alternatively, the rate variability indices may be calculated as other statistical measures of the amount of variance or change in the rates of the ventricular waveforms 200, 300.

In another example, the evaluation processor 108 (shown in FIG. 1) compares amplitude indices 220, 320 of the ventricular waveforms 200, 300 to determine if the clinical and induced VT events are a common type of VT event. The amplitude indices 220, 320 represent magnitudes or amplitudes of the ventricular waveforms 200, 300. In the illustrated embodiment, the amplitude indices 220, 320 are measured at or near peaks of the QRS complexes 206, 306 of the ventricular waveforms 200, 300. For example, the amplitude indices 220, 320 may represent increases of the R-waves 210, 310 above corresponding baselines 222, 322 of the ventricular waveforms 200, 300.

The evaluation processor 108 (shown in FIG. 1) may compare waveform morphology indices of the ventricular waveforms 200, 300 to determine if the clinical and induced VT events are a common type of VT event. A waveform morphology index represents a measurement of a segment of the ventricular waveforms 200, 300 that indicates a size or shape of the waveform segment. For example, a measurement of a slope or rate of change in a segment of the ventricular waveform 200 or 300 or a width of a segment of the ventricular waveform 200 or 300 may be a waveform morphology index.

The evaluation processor 108 (shown in FIG. 1) may perform frequency analysis of the ventricular waveforms 200, 300 to measure or calculate frequency indices of one or more segments of the ventricular waveforms 200, 300. The frequency indices may be compared to determine if the clinical and induced VT events are a common type of VT event. Frequency indices may include frequency-based features of the ventricular waveforms 200, 300, such as measurements of a segment of the ventricular waveforms 200, 300 that indicate frequency contents of the waveform segment. By way of example only, frequency-based features may include dominant frequencies, frequency widths, and the like of a waveform morphology in a segment of the ventricular waveform 200, 300 or a VT rate of a segment of the ventricular waveform 200, 300.

The evaluation processor 108 (shown in FIG. 1) may compare other cardiac indices such as LAP and/or electrical impedance vectors measured between predetermined combinations of electrodes 118, 120, 122, 124, 126, 128, 130, 132, 134, 146, 148, 150 (shown in FIG. 1) and/or the housing 110 (shown in FIG. 1). The LAP and/or impedance vectors are measured during and/or following the clinical and induced VT events and compared between the clinical and induced VT events. Differences between the LAP measurements and/or electrical impedance vectors may indicate if the clinical and induced VT events are the common type of VT event.

The evaluation processor 108 (shown in FIG. 1) may compare cardiac parameters obtained from the sensors 136, 138, 140, 142 (shown in FIG. 1), such as blood pressure measurements, blood oxygen content measurements, volume measurements of the heart 104 (shown in FIG. 1), and the like, obtained during and/or following the clinical and induced VT events. Differences in one or more of the measurements may indicate if the clinical and induced VT events are the common type of VT event.

In one embodiment, the IMD 102 (shown in FIG. 1) may apply a pacing regimen to the heart 104 (shown in FIG. 1) during the clinical and induced VT events. For example, the IMD 102 may deliver stimulus pulses to the heart 104 at a predetermined rate and/or magnitude during the clinical and induced VT events. One or more of the cardiac indices and/or parameters described above may be measured during and/or following application of the pacing regimen to the heart 104. By way of example only, an anti-tachycardia pacing (ATP) therapy may be applied to the heart 104 during the clinical and induced VT events and when the cardiac indices and/or cardiac parameters are measured. The cardiac indices and/or cardiac parameters may be measured during and/or following delivery of the ATP therapy. In one embodiment, IEGM or activation pattern characterization also can be performed during pace-mapping from various sites or locations in the ventricles.

The evaluation processor 108 (shown in FIG. 1) identifies differences in the cardiac indices between cardiac signals obtained during and/or following the clinical VT event and cardiac signals obtained during and/or following the induced VT event. The evaluation processor 108 also identifies differences in the cardiac parameters measured during and/or following the clinical VT event and cardiac parameters measured during and/or following the induced VT event. The evaluation processor 108 determines if the clinical VT event and the induced VT event are a common type of VT event based on the differences in the cardiac indices and/or the differences in the cardiac parameters. For example, the evaluation processor 108 may calculate differences in the VT cycle lengths 216, 316 to determine if the clinical VT event and the induced VT event are a common type of VT event. The evaluation processor 108 may also calculate differences in blood oxygen contents measured during and/or following the clinical VT event with blood oxygen contents measured during and/or following the induced VT event to determine if the clinical VT event and the induced VT event are a common type of VT event. If the differences in the cardiac indices and/or cardiac parameters between the clinical VT event and the induced VT event exceed the predetermined thresholds, then the differences may indicate that the clinical and induced VT events are not a common type of VT event. Conversely, if the differences do not exceed the thresholds, then the differences may indicate that the clinical and induced VT events are a common type of VT event.

In another embodiment, the IMD 102 (shown in FIG. 1) determines if the clinical VT event and the induced VT event are a common type of VT event. The IMD 102 may calculate differences in the cardiac signals obtained during and/or following the induced VT event with the cardiac signals obtained during and/or following the clinical VT event. The IMD 102 may receive the cardiac parameters from the measured during and/or following the clinical VT event and the cardiac parameters measured during and/or following the induced VT event from the sensors 136, 138, 140, 142 (shown in FIG. 1). The IMD 102 may calculate differences between the cardiac parameters from the clinical VT event and the induced VT event. Based on the differences in the cardiac signals and the differences in the cardiac parameters, the IMD 102 determines if the clinical VT event and the induced VT event are a common type of VT event, similar to as described above.

Several uncorrelated cardiac indices and cardiac parameters may be compared between the clinical and induced VT events to determine if the clinical and induced VT events are similar. For example, amplitude indices 220, 320 may be compared between the clinical and induced VT events and heart volume measurements from the PPG sensor 140 (shown in FIG. 1) may be compared between the clinical and induced VT events. Different and/or additional cardiac signals and cardiac parameters may be compared. The cardiac signals may be uncorrelated to the cardiac parameters, and vice-versa, if the cardiac signals do not change based on a change in the cardiac parameters. The evaluation processor 108 (shown in FIG. 1) may compare differences in several uncorrelated cardiac signals and cardiac parameters between the clinical and induced VT events with several corresponding thresholds.

The number of cardiac signals and cardiac parameters having differences between the clinical and induced VT events that do not exceed the thresholds may be used by the evaluation processor 108 (shown in FIG. 1) to determine if the clinical and induced VT events are a common type of VT event. For example, if at least a predetermined number of the differences in the cardiac signals and cardiac parameters do not exceed the corresponding thresholds, then the differences in the cardiac signals and cardiac parameters between the clinical and induced VT events may be relatively small. As a result, the evaluation processor 108 may determine that the clinical and induced VT events are similar and are a common type of VT event. Conversely, if fewer than the predetermined number of differences in the cardiac signals and cardiac parameters do not exceed the corresponding thresholds, then the differences in the cardiac signals and cardiac parameters between the clinical and induced VT events may be relatively large. As a result, the evaluation processor 108 may determine that the clinical and induced VT events are not similar and are not a common type of VT event.

Returning to the discussion of the system 100 shown in FIG. 1, the evaluation processor 108 may be coupled with a display device 144. The display device 144 may be a monitor, such as a CRT, LCD, and the like monitor. The display device 144 may present a physician with the cardiac indices and/or cardiac parameters obtained by the system 100. For example, the display device 144 may display the values of the cardiac indices and/or cardiac parameters and the differences between the cardiac indices and/or cardiac parameters between the clinical and induced VT events. The values of the cardiac indices, cardiac parameters, and associated differences may be displayed in real time. For example, the cardiac indices, cardiac parameters, and differences between the cardiac indices and parameters of the clinical and induced VT events may be displayed on the display device 144 as the clinical indices and parameters of the induced VT event are obtained and/or calculated.

In one embodiment, the display device 144 is part of a mapping system that visually characterizes the induced VT event. For example, the display device 144 may map out an image of the rotor or trigger locations of the induced VT event, the electric conduction pathways of the induced VT event, and the like, onto an image of the heart 104. By way of example only, the display device 144 may be configured to provide the visual representations of the heart 104 and of VT events in a manner similar to the Ensite NavX™ system provided by St. Jude Medical. The cardiac indices and cardiac parameters obtained during and/or following the clinical and induced VT events and/or the differences in the cardiac indices and cardiac parameters may be used by the mapping system to identify the sources and pathways of the induced VT event. For example, cardiac indices that represent impedance vectors crossing through the heart 104 may be used to determine if a VT trigger or pathway passes through the myocardium in the same area that the vectors cross the myocardium.

The cardiac indices and cardiac parameters may be used to visually display the sources and pathways of the induced VT event during and/or following application of ablation to the heart 104, such as ablation procedures for VT events, superventricular tachycardia (SVT) events, and the like. The visual display of the heart 104 and sources and pathways of the induced VT event may be updated as additional cardiac indices and cardiac parameters, and differences in the cardiac indices and cardiac parameters, are obtained.

In one embodiment, the evaluation processor 108 determines the rotor or trigger locations of the induced VT event, the electric conduction pathways of the induced VT event, and the like, based on the cardiac indices and cardiac parameters obtained during and/or following the clinical and induced VT events and/or the differences in the cardiac indices and cardiac parameters. The rotor and/or trigger locations are communicated to the IMD 102 and stored in the memory 528 (shown in FIG. 5) of the IMD 102. The IMD 102 may use the rotor and/or trigger locations to characterize future clinical VT events. For example, the IMD 102 may monitor one or more of the same cardiac indices or cardiac parameters during a future clinical VT event and compare the cardiac indices or cardiac parameters with the cardiac indices or cardiac parameters of the induced VT event. The comparisons of the cardiac indices from the future clinical VT event with the cardiac indices of the induced VT event and/or of the cardiac parameters from the future clinical VT event with the cardiac parameters of the induced VT event may be used to characterize the future clinical VT event as being the same type or different type of VT event. For example, similar to the characterization of the induced VT event and clinical VT event as being a common type of event, the cardiac indices and cardiac parameters may be used to determine if the induced VT event and a future clinical VT event are a common type of event.

The evaluation processor 108 may communicate the locations in the heart 104 where ablative energy was applied to the IMD 102. The locations where ablative energy was applied are referred to as ablation locations. The ablation locations are used by the IMD 102 to characterize future clinical VT events as being a common or different type of VT event as the induced VT event. For example, during a future clinical VT event, the IMD 102 may monitor cardiac indices that represent impedance vectors crossing through the ablation locations stored in the memory 528 (shown in FIG. 5) of the IMD 102. The IMD 102 may communicate the cardiac indices of the future clinical VT event to the evaluation processor 108. The evaluation processor 108 compares the cardiac indices of the future clinical VT event with the same or similar cardiac indices measured during the induced VT event. Based on the differences between the cardiac indices, the evaluation processor 108 may characterize the future clinical VT event and the induced VT event as a common type of VT event or as different type of VT events.

The IMD 102 may monitor precursor parameters related to the onset of clinical VT events. Precursor parameters are measurements of cardiac function that are obtained prior to a clinical VT event. For example, the IMD 102 may record a moving window of cardiac signals obtained by the electrodes 118, 120, 122, 124, 126, 128, 130, 132, 134, 146, 148, 150. When a clinical VT event is detected by the IMD 102, the IMD 102 may save the cardiac signals that occurred prior to or leading up to onset of the clinical VT event for analysis. The IMD 102 may communicate the cardiac signals occurring prior to the clinical VT event to the external device 106 as precursor parameters.

The external device 106 communicates the precursor parameters to the evaluation processor 108. The evaluation processor 108 examines the precursor parameters to identify potential causes or sources of the clinical VT event. For example, the evaluation processor 108 may examine the cardiac signals to determine if the heart 104 was exhibiting signs of an abnormal heart rate, such as bradycardia or tachycardia, prior to the clinical VT event. The evaluation processor 108 may analyze the cardiac signals to determine the exercise or activity level of the heart 104 based on the heart rate prior to the clinical VT event. In another example, electrical impedance vectors between predetermined combinations of the electrodes 118, 120, 122, 124, 126, 128, 130, 132, 134, 146, 148, 150 and/or housing 110 obtained prior to the clinical VT event may be examined. Other precursor parameters may be measured by the sensors 136, 138, 140, 142. For example, the sensors 136, 138, 140, 142 may be capable of measuring neural activity of the patient, acoustic noises of the heart 104, respiration patterns of the patient, and the like, prior to the onset of the clinical VT event.

The precursor parameters are used by the evaluation processor 108 to identify sources or causes of the clinical VT event. For example, the evaluation processor 108 may examine changes in electrical impedance vectors prior to and during and/or following the clinical VT event to locate premature ventricular contractions and sources and/or pathways of the clinical VT event in the heart 104. The sources and/or pathways may be displayed on the display device 144 and used to guide the physician that applies an ablation procedure to the heart 104.

During the induced VT event, the evaluation processor 108 may compare cardiac signals obtained by the electrodes 118, 120, 122, 124, 126, 128, 130, 132, 134, 146, 148, 150 with cardiac signals obtained by ECG electrodes externally positioned on the patient. For example, the evaluation processor 108 may receive cardiac signals from the IMD 102 and the ECG sensor 142 and compare the cardiac signals to determine whether the induced VT event is a focal VT event or a reentrant VT event. The focal and reentrant VT events may be distinguished by comparing activation times associated with ventricular activity as measured by one or more ventricular electrodes 118, 120, 130 and as measured by one or more ECG sensors 142 following application of stimulus pulses to the left and/or right ventricles. For example, the IMD 102 may apply a stimulus pulse to the right ventricle. The IMD 102 measures an activation time between application of the stimulus pulse and detection of right ventricular activity using one or more of the electrodes 118, 120, 130 positioned in the right ventricle.

The evaluation processor 108 also measures an activation time between application of the stimulus pulse and detection of right ventricular activity using one or more of the external electrodes of the ECG sensor 142. The evaluation processor 108 compares the activation times measured using the IMD 102 and the ECG sensor 142 to determine if the VT event is a focal or reentrant VT event. In one embodiment, if a difference between the activation times is approximately 60% or less than the VT cycle length 216 or 316 (shown in FIGS. 2 and 3), then the evaluation processor 108 may determine that the VT event is a focal VT event. Alternatively, a different threshold may be used to compare with the difference in activation times, such as 70%, 50%, or 40% or less than the VT cycle length 216 or 316. If the difference between activation times is approximately the same time period as the VT cycle length 216 or 316, then the evaluation processor 108 may determine that the VT event is a reentrant VT event. For example, the evaluation processor 108 may classify the VT event as a reentrant VT event if the difference in activation times is larger than 60% of the VT cycle length 216 or 316. Alternatively, the evaluation processor 108 may classify the VT event as a reentrant VT event if the difference in activation times is larger than a different percentage of the VT cycle length 216 or 316.

The IMD 102 may examine the effectiveness of a pacing regimen in stopping or slowing the induced VT event and use the same pacing regimen to stop or slow future clinical VT events that are similar to the induced VT event. The IMD 102 applies stimulus pulses to the heart 104 according to a pacing regimen and senses cardiac signals of the heart 104 during the induced VT event. The cardiac signals are communicated to the evaluation processor 108. The evaluation processor 108 examines the cardiac signals to determine if the pacing regimen is effective in slowing or stopping the induced VT event. For example, the evaluation processor 108 may examine the rate of ventricular contraction during the induced VT event when the pacing regimen is applied to the heart 104 in order to determine if the pacing regimen is effective in ending the induced VT event. Alternatively, the IMD 102 may determine if the pacing regimen is effective in stopping or slowing the induced VT event.

If the pacing regimen is effective in ending the induced VT event, the evaluation processor 108 communicates the cardiac signals and the effective pacing regimen to the IMD 102. The IMD 102 may store the cardiac signals and the effective pacing regimen in the memory 528 (shown in FIG. 5) of the IMD 102. During a future VT event that occurs after the induced VT event, the IMD 102 senses cardiac signals of the heart 104. For example, if the induced VT event occurred during delivery of an ablation procedure, the IMD 102 may sense cardiac signals during a future post-ablation VT event. The IMD 102 may compare the cardiac signals from the post-ablation VT event with the cardiac signals stored in the memory 528 (shown in FIG. 5) to determine if the two cardiac signals correspond with or match each other. For example, the IMD 102 may compare cardiac indices of the cardiac signals obtained during and/or following the induced VT event and the post-ablation VT event. If the differences between the cardiac indices do not exceed one or more predetermined thresholds, then the post-ablation VT event may be similar to the induced VT event. If the post-ablation VT event is similar to the induced VT event, the IMD 102 applies the pacing regimen that was effective in slowing or stopping the induced VT event to slow or stop the post-ablation VT event. For example, the IMD 102 may determine that the cardiac signals of the induced and post-ablation VT events are similar enough that the pacing regimen that was effective to stop the induced VT event should be used to stop the post-ablation VT event.

Figure 4A:
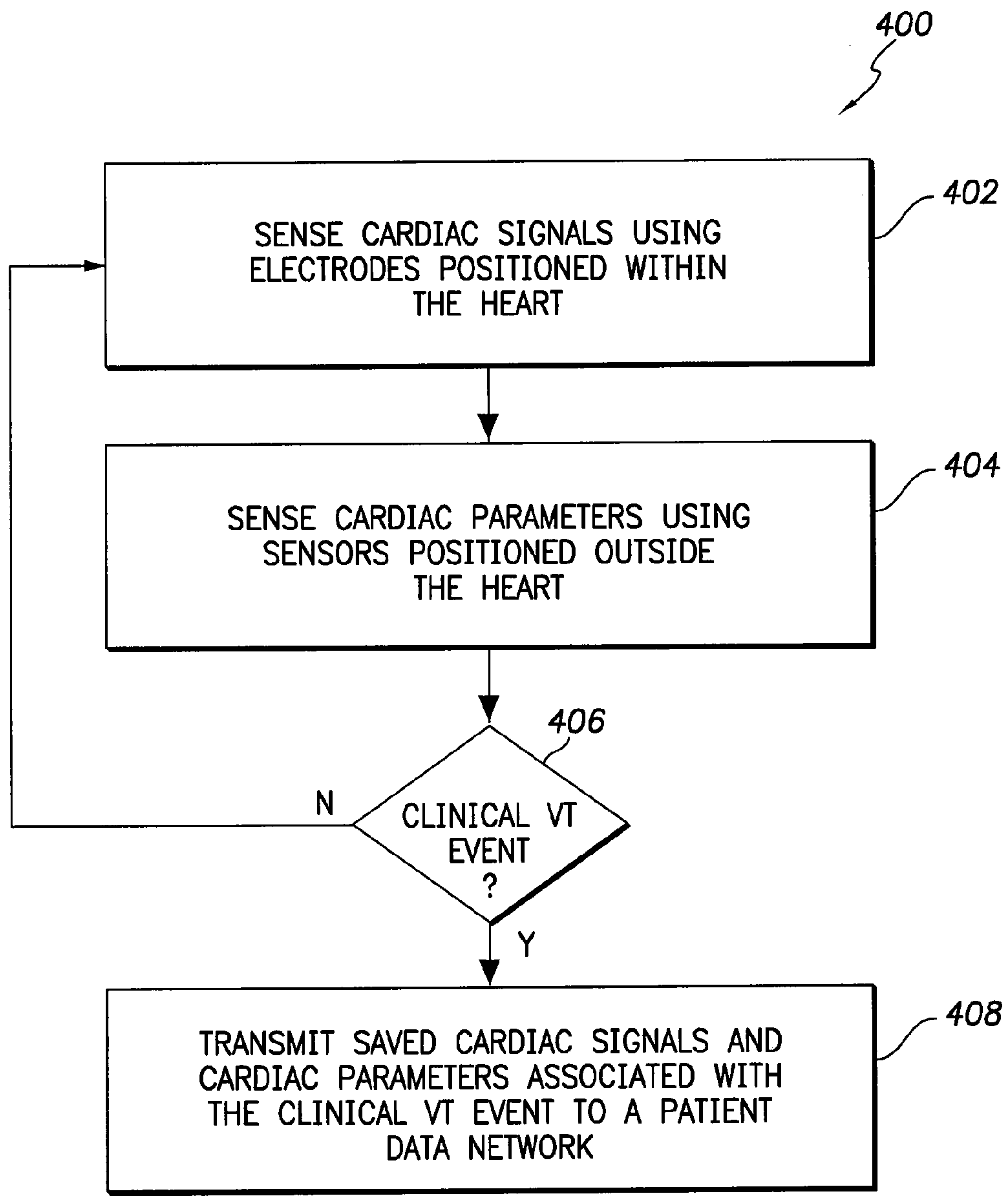
FIGS. 4A and 4B include a flowchart for a method of comparing VT events of a heart to apply an ablation procedure to the heart in accordance with one embodiment.
Figure 4B:
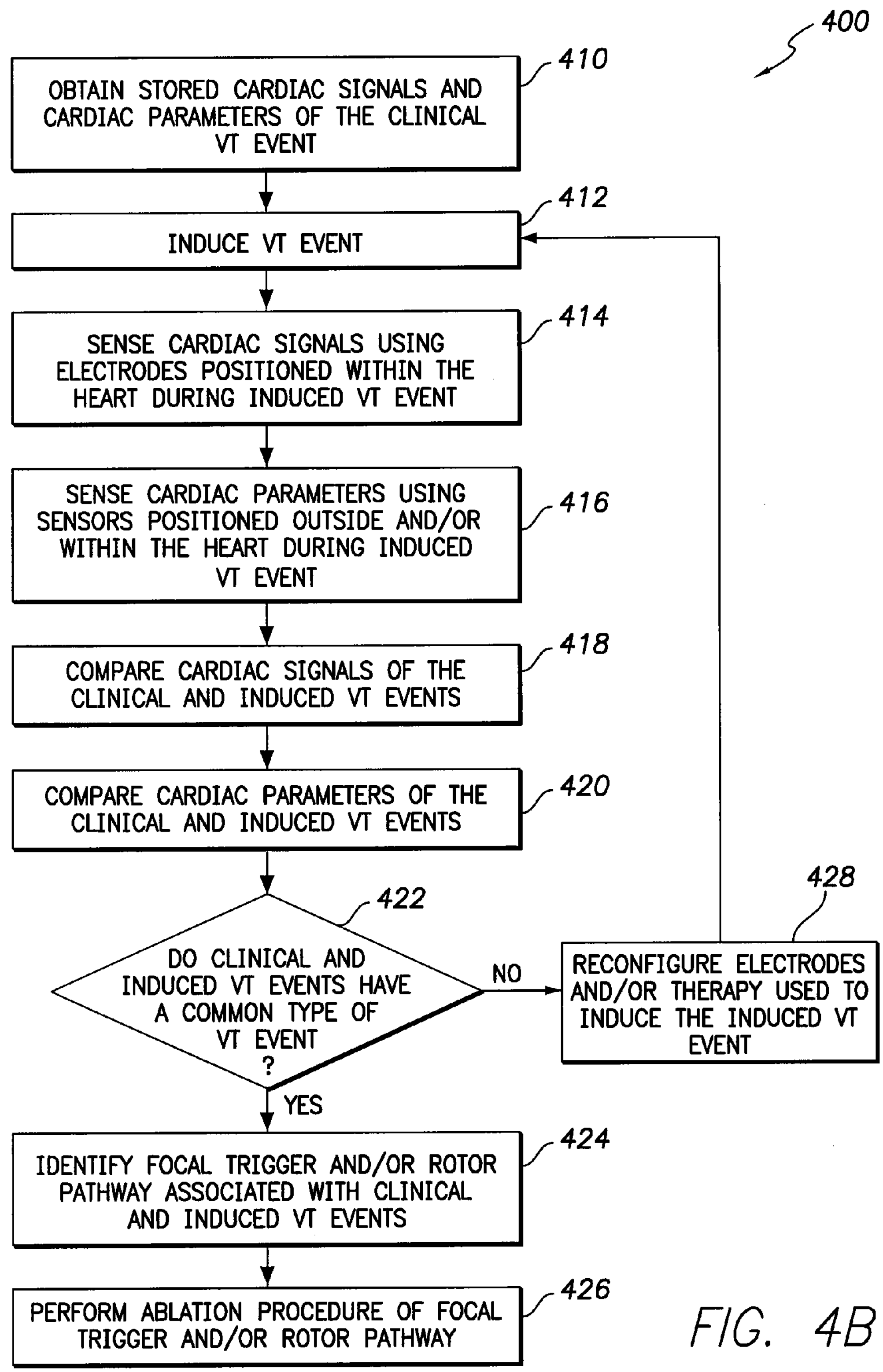

FIGS. 4A and 4B include a flowchart for a method 400 of comparing VT events of the heart 104 (shown in FIG. 1) to apply an ablation therapy to the heart 104 in accordance with one embodiment. With respect to FIG. 4A, at 402, cardiac signals of the heart 104 are sensed by one or more electrodes 118, 120, 122, 124, 126, 128, 130, 132, 134, 146, 148, 150 (shown in FIG. 1) positioned within the heart 104.

At 404, cardiac parameters of the heart 104 (shown in FIG. 1) are measured by one or more sensors 136, 138, 140, 142 (shown in FIG. 1) that are positioned outside the heart 104.

At 406, the cardiac signals and/or cardiac parameters are examined to determine if the cardiac signals and/or cardiac parameters were obtained during and/or following a clinical VT event of the heart 104 (shown in FIG. 1). In one embodiment, one or more cardiac indices of the cardiac signals may be examined. For example, one or more of a VT cycle length 216, 316 (shown in FIGS. 2 and 3), a variability in the VT cycle lengths 216, 316, a rate of ventricular contraction, a variability in the rate of ventricular contraction, an amplitude of ventricular waveform segments, a waveform morphology index, a LAP measurement, electrical impedance vector, and the like, of the cardiac signals may be compared to one or more predetermined thresholds to determine if the cardiac signals represent a VT event. By way of non-limiting example only, the rate of ventricular contractions may be compared to a threshold. If the rate exceeds the threshold, then the cardiac signals indicate that the cardiac signals represent or are associated with a clinical VT event. As a result, flow of the method 400 proceeds to 408. Alternatively, if the cardiac signals do not represent a clinical VT event, then flow of the method 400 proceeds back to 402.

At 408, the cardiac signals and cardiac parameters associated with the clinical VT event are transmitted to a patient data network. For example, the cardiac signals and cardiac parameters may be communicated to a server 702 (shown in FIG. 7) for storage in a database 704 (shown in FIG. 7) of a patient data network 700 (shown in FIG. 7). The cardiac signals and cardiac parameters are stored for later retrieval and comparison to cardiac signals and cardiac parameters obtained during and/or following an induced VT" event. Flow of the method 400 continues from 408 shown in FIG. 4A to 410 shown in FIG. 4B. The flow of the method 400 between 408 and 410 may be continuous or may be interrupted by a passage of time. For example, one or more days or weeks may extend between 408 and 410.

At 410 in FIG. 4B, the cardiac signals and cardiac parameters associated with the clinical VT event are obtained from the patient data network. For example, the evaluation processor 106 (shown in FIG. 1) may retrieve the cardiac signals and cardiac parameters associated with the clinical VT event from the server 702 (shown in FIG. 7) and the database 704 (shown in FIG. 7) of the patient data network 700 (shown in FIG. 7).

At 412, a VT event is induced. For example, stimulus pulses may be delivered to the heart 104 (shown in FIG. 1) by one or more of the electrodes 118, 120, 122, 124, 126, 128, 130, 132, 134, 146, 148, 150 (shown in FIG. 1). The stimulus pulses may be delivered to cause a VT event, or an induced VT event.

At 414, cardiac signals are sensed during and/or following the induced VT event. As described above, one or more of the electrodes 118, 120, 122, 124, 126, 128, 130, 132, 134, 146, 148, 150 (shown in FIG. 1) may sense cardiac signals of the heart 104 (shown in FIG. 1) during and/or following the induced VT event.

At 416, cardiac parameters are sensed during and/or following the induced VT event. As described above, one or more sensors 136, 138, 140, 142 (shown in FIG. 1) may measure the cardiac parameters during and/or following the induced VT event.

At 418, the cardiac signals of the induced VT event are compared to the cardiac signals of the clinical VT event. For example, one or more indices of the cardiac signals of the induced VT event may be compared to one or more indices of the cardiac signals of the clinical VT event to identify differences between the cardiac signals.

At 420, the cardiac parameters of the induced VT event are compared to the cardiac parameters of the clinical VT event. For example, the cardiac parameters may be compared to identify differences between the cardiac parameters associated with the clinical and induced VT events.

At 422, the differences in the cardiac signals and the differences in the cardiac parameters are examined to determine if the clinical and induced VT events have a common type of VT event. For example, one or more differences in the cardiac signals and the cardiac parameters may be compared to predetermined thresholds. If the differences in the cardiac signals and/or cardiac parameters are relatively small such that the differences do not exceed the thresholds, then the differences in the cardiac signals and the differences in the cardiac parameters may indicate that the induced VT event and the clinical VT event have a common type of VT event, or are a common type of VT event. Conversely, if the differences in the cardiac signals and/or cardiac parameters are relatively large, then the differences in the cardiac signals and the differences in the cardiac parameters may indicate that the induced VT event and the clinical VT event do not have a common type of VT event, or are not a common type of VT event.

If the differences in the cardiac signals and the differences in the cardiac parameters indicate that the clinical and induced VT events have a common type of VT event, then flow of the method 400 proceeds to 424. Alternatively, if the differences in the cardiac signals and the differences in the cardiac parameters do not indicate that the clinical and induced VT events have a common type of VT event, then flow of the method 400 proceeds to 428.

At 424, one or more focal triggers and/or rotor pathways associated with the clinical and induced VT events are identified. As described above, a focal trigger and/or rotor pathway of a VT event affects cardiac signals sensed by the electrodes 118, 120, 122, 124, 126, 128, 130, 132, 134, 146, 148, 150 (shown in FIG. 1) positioned relatively close to the focal trigger and/or rotor pathway. The cardiac signals of the clinical and/or induced VT events may be examined to determine which of the electrodes 118, 120, 122, 124, 126, 128, 130, 132, 134, 146, 148, 150 sensed cardiac signals that were affected or impacted by the VT event. For example, the cardiac signals sensed by the electrodes located closer to a focal trigger or rotor pathway may be altered more than the cardiac signals sensed by the electrodes 118, 120, 122, 124, 126, 128, 130, 132, 134, 146, 148, 150 located farther from the focal trigger or rotor pathway. Based on which electrodes have cardiac signals that were affected by the VT event, the IMD 102 (shown in FIG. 1) and/or external device 106 (shown in FIG. 1) may discern the approximate location of the focal trigger and/or rotor pathway in the heart 104 (shown in FIG. 1).

At 426, an ablation procedure is applied to the areas of the heart 104 (shown in FIG. 1) where the focal trigger and/or rotor pathways are located. The locations of the focal trigger and/or rotor pathways identified above may be displayed in real-time to a physician who ablates the locations. As described above, the ablation procedure may prevent future VT events from occurring.

Returning to the discussion of 422, if the clinical and induced VT events do not have a common VT event, then, at 428, one or more of the electrodes 118, 120, 122, 124, 126, 128, 130, 132, 134, 146, 148, 150 (shown in FIG. 1) and/or stimulus therapy used to induce the induced VT event are reconfigured. For example, if the induced VT event is dissimilar to the clinical VT event, then the stimulus pulses applied at 412 may be modified by changing the strength and/or location where the stimulus pulses are delivered. As another example, the electrodes 118, 120, 122, 124, 126, 128, 130, 132, 134, 146, 148, 150 used to sense the cardiac signals during and/or following the induced VT event may be reconfigured by using different electrodes to sense other cardiac signals. Flow of the method 400 returns to 412 where another VT event is induced. This induced VT event may be induced using different electrodes 118, 120, 122, 124, 126, 128, 130, 132, 134, 146, 148, 150 to sense cardiac signals, by delivering different stimulus pulses, and/or by changing the locations where the stimulus pulses are delivered to the heart 104 (shown in FIG. 1).

Figure 5:
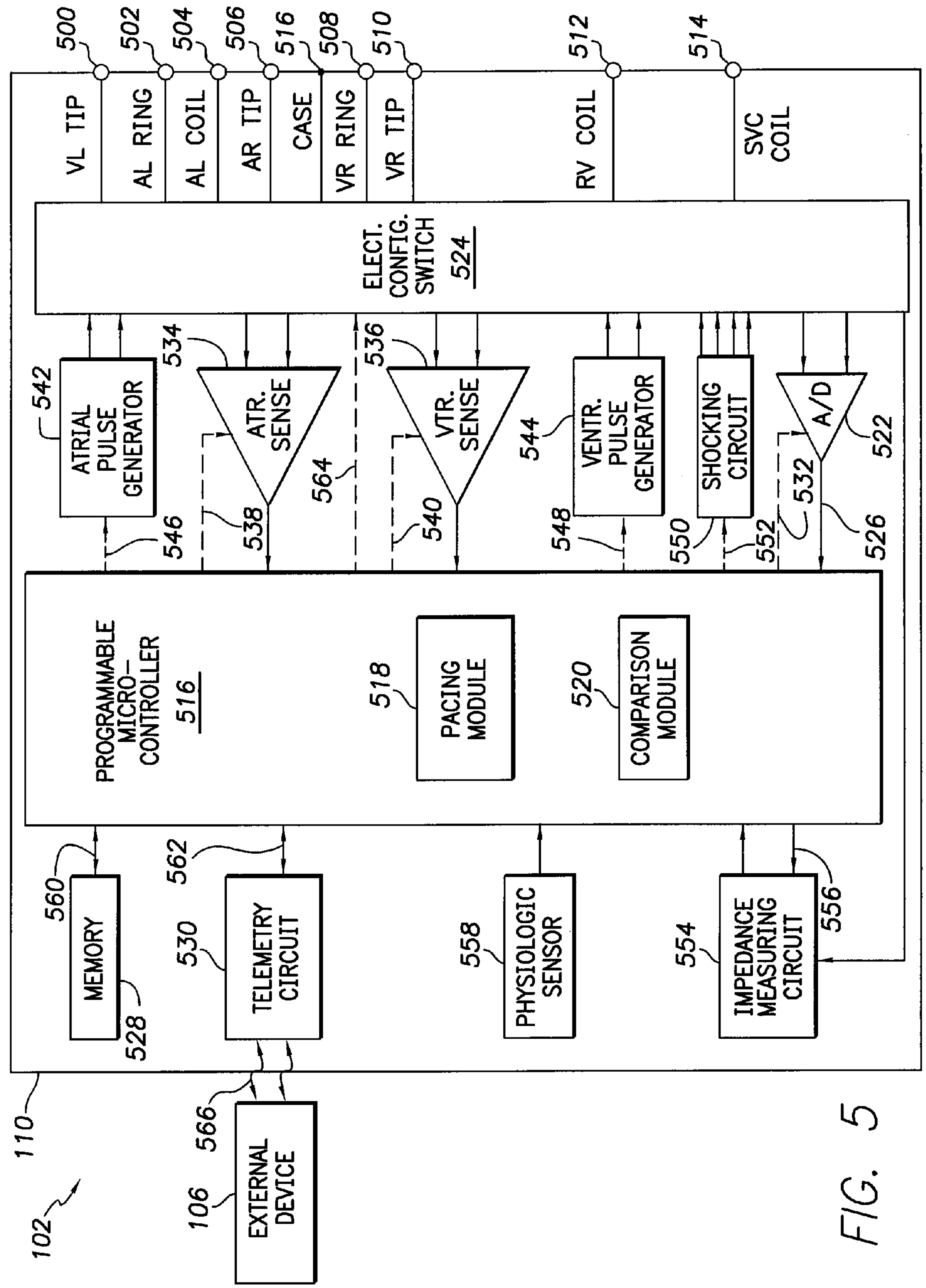
FIG. 5 is a block diagram of exemplary internal components of the implantable medical device shown in FIG. 1 in accordance with one embodiment.

FIG. 5 is a block diagram of exemplary internal components of the IMD 102 in accordance with one embodiment. The IMD 102 includes the housing 110 that has an LV tip input terminal ($V_L$ TIP) 500, an LA ring input terminal ($A_L$ RING) 502, an LA coil input terminal ($A_L$ COIL) 504, an RA tip input terminal ($A_R$ TIP) 506, an RV ring input terminal ($V_R$ RING) 508, an RV tip input terminal ($V_R$ TIP) 510, an RV coil input terminal 512, and an SVC coil input terminal 514. A case input terminal 516 may be coupled with the housing 110. The input terminals 500, 502, 504, 506, 508, 510, 512, 514 may be electrically coupled with the electrodes 118, 120, 122, 124, 126, 128, 130, 132, 134, 146, 148, 150 (shown in FIG. 1).

The IMD 102 includes a programmable controller 516 that controls the operations of the IMD 102. The controller 516 (also referred to herein as a processor, processor module, or unit) typically includes a microprocessor, or equivalent control circuitry, and may be specifically designed for controlling the delivery of stimulation therapy to the heart 104 (shown in FIG. 1) and monitoring cardiac signals of the heart 104, and may further include RAM or ROM memory, logic and timing circuitry, state machine circuitry, and I/O circuitry. The controller 516 may include one or more modules and processors configured to perform one or more operations described above.

A pacing module 518 directs the IMD 102 to apply stimulus pulses to the heart 104 (shown in FIG. 1) according to one or more pacing therapies. The pacing module 518 may obtain the pacing therapies from the memory 528 of the IMD 102 and direct the IMD 102 to deliver stimulus pulses according to the pacing therapies. Different pacing therapies direct the IMD 102 to supply the stimulus pulses using different electrodes 118, 120, 122, 124, 126, 128, 130, 132, 134, 146, 148, 150 (shown in FIG. 1) and/or at different frequencies or rates.

A comparison module 520 determines which pacing regimen to apply to the heart 104 (shown in FIG. 1). The comparison module 520 may compare cardiac signals of a current VT event with cardiac signals of a previous VT event, such as the induced VT event. The comparison module 520 may obtain the cardiac signals from the previous induced VT event from the memory 528. The comparison module 520 compares the cardiac signals of the current and induced VT events to determine if the current and induced VT events are similar. As described above, the comparison module 520 may examine differences between cardiac indices of the cardiac signals of the current and induced VT events. If the differences are smaller than one or more predetermined thresholds, then the comparison module 520 may determine that the current and induced VT events are similar.

If the comparison module 520 determines that the current and induced VT events are similar and if a pacing regimen is associated with the induced VT event, then the comparison module 520 may direct the pacing module 518 to apply the pacing regimen. For example, if a pacing regimen was effective in slowing or stopping the induced VT event and the comparison module 520 determines that a current VT event is similar to the induced VT event, then the comparison module 520 may direct the pacing module 518 to apply the pacing regimen to the heart 104 (shown in FIG. 1).

An atrial sensing circuit 534 and a ventricular sensing circuit 536 may be selectively coupled to the leads 112, 114, 116 (shown in FIG. 1) of the IMD 102 through the switch 524 for detecting the presence of cardiac activity in the chambers of the heart 104 (shown in FIG. 1). The sensing circuits 534, 536 may sense the cardiac signals that are analyzed by the controller 516. Control signals 538, 540 from the controller 516 direct output of the sensing circuits 534, 536 to the controller 516.

The controller 516 receives the cardiac signals from the electrodes 118, 120, 122, 124, 126, 128, 130, 132, 134, 146, 148, 150 (shown in FIG. 1) via an analog-to-digital (A/D) data acquisition system 522. The cardiac signals are sensed by the electrodes 118, 120, 122, 124, 126, 128, 130, 132, 134, 146, 148, 150 and communicated to the data acquisition system 522. The cardiac signals are communicated through the input terminals 500, 502, 504, 506, 508, 510, 512, 514, 516 to an electronically configured switch bank, or switch, 524 before being received by the data acquisition system 522. The switch 524 closes and opens switches to provide electrically conductive paths between the circuitry of the IMD 102 and the input terminals 500, 502, 504, 506, 508, 510, 512, 514, 516 in response to a control signal 564. The data acquisition system 522 converts the raw analog data of the signals obtained by the electrodes 118, 120, 122, 124, 126, 128, 130, 132, 134, 146, 148, 150 into digital signals 526 and communicates the signals 526 to the controller 516. A control signal 532 from the controller 516 determines when the data acquisition system 522 acquires signals, stores the signals 526 in the memory 528, or transmits data to the external device 106 via a telemetry circuit 530.

An atrial pulse generator 542 and a ventricular pulse generator 544 generate pacing stimulation pulses for delivery by the leads 112, 114, 116 (shown in FIG. 1) and the electrodes 118, 120, 122, 124, 126, 128, 130, 132, 134, 146, 148, 150 (shown in FIG. 1) according to directions from the pacing module 518. The atrial and ventricular pulse generators 542, 544 may include dedicated, independent pulse generators, multiplexed pulse generators, or shared pulse generators. The pulse generators 542, 544 are controlled by the pacing module 518 via appropriate control signals 546, 548, respectively, to trigger or inhibit the stimulation pulses.

The pacing module 518 controls a shocking circuit 550 by way of a control signal 552. The shocking circuit 550 generates shocking pulses that are applied to the heart 104 (shown in FIG. 1) through at least two shocking electrodes, such as the RV coil electrode 122 (shown in FIG. 1), the LA coil electrode 134 (shown in FIG. 1), and/or the SVC coil electrode 124 (shown in FIG. 1).

An impedance measuring circuit 554 is enabled by the controller 516 via a control signal 556. The impedance measuring circuit 554 may be electrically coupled to the switch 524 so that an impedance vector between predetermined combinations of electrodes 118, 120, 122, 124, 126, 128, 130, 132, 134, 146, 148, 150 (shown in FIG. 1) and/or the housing 110 may be obtained. As described above, the impedance vectors between predetermined combinations of the electrodes 118, 120, 122, 124, 126, 128, 130, 132, 134, 146, 148, 150 and/or the housing 110 may be obtained during and/or following clinical and induced VT events to determine if the clinical and induced VT events are a common type of VT event.

The IMD 102 includes one or more physiologic sensors 558 that may be used to adjust pacing stimulation rate according to the exercise state of the patient. For example, a pacing stimulation rate that is selected by the pacing module 518 may be adjusted by the physiologic sensor 558 based on the exercise state of the patient. Other examples of possible physiologic sensors 558 include a blood pressure sensor, a blood oxygen sensor and a photoplethysmograph sensor The memory 528 may be embodied in a tangible and non-transitory computer-readable storage medium such as a ROM, RAM, flash memory, or other type of memory. The controller 516 is coupled to the memory 528 by a suitable data/address bus 560. The memory 528 may store programmable operating parameters, thresholds, cardiac signals sensed by the IMD 102 and/or external device 106 (shown in FIG. 1), effective pacing therapies, and the like, in order to customize the operation of IMD 102 to suit the needs of a particular patient. The operating parameters of the IMD 102 and thresholds may be non-invasively programmed into the memory 528 through the telemetry circuit 530 in communication with the external device 106. The telemetry circuit 530 is activated by the controller 516 by a control signal 562. The telemetry circuit 530 allows intra-cardiac electrograms, cardiac waveforms of interest, thresholds, cardiac signals, cardiac parameters, pacing therapies, cardiac indices, status information, and the like, to be sent to the external device 106 through an established communication link 564.

Figure 6:
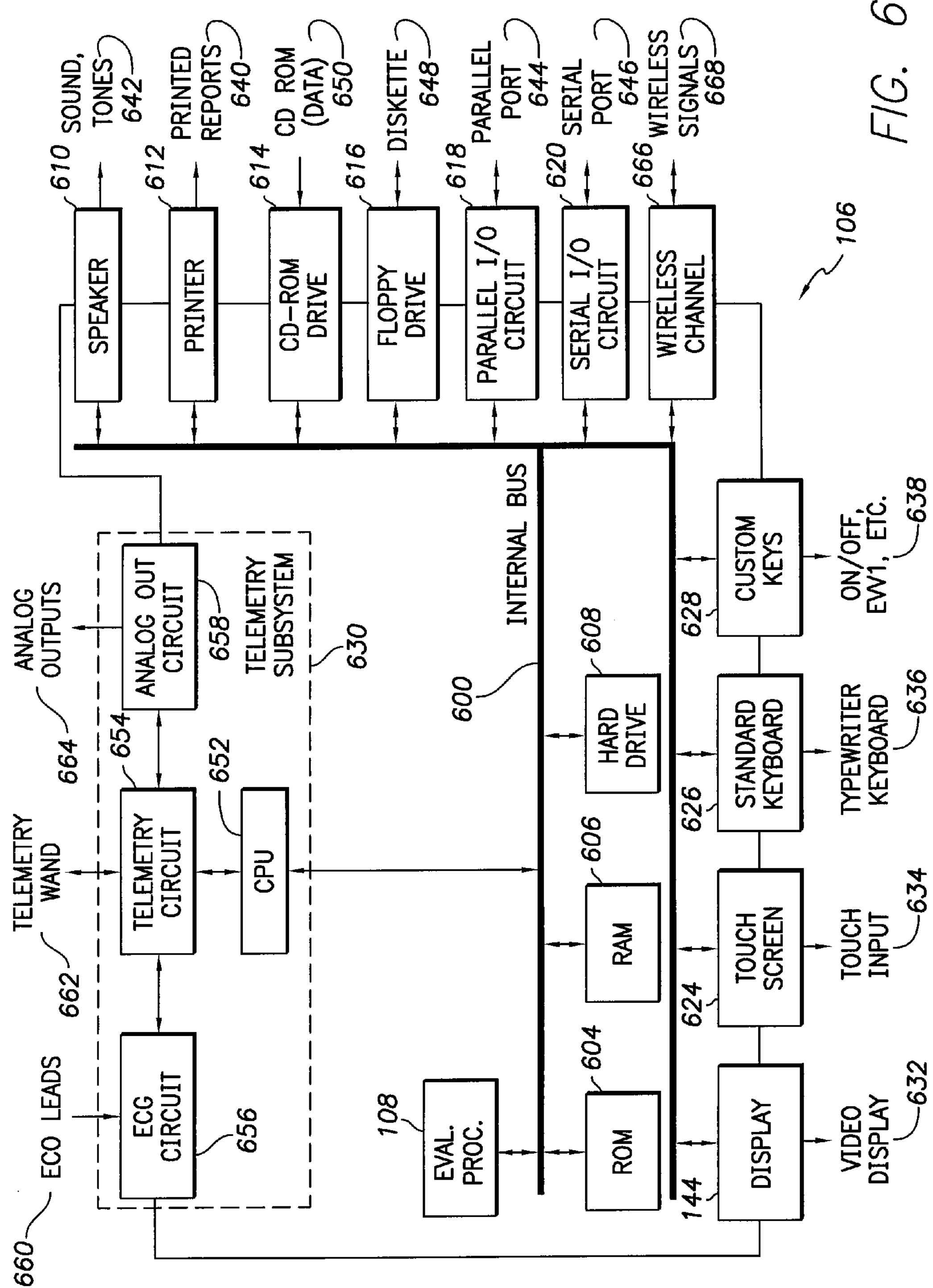
FIG. 6 illustrates a functional block diagram of an external device shown in FIG. 1 in accordance with one embodiment.

FIG. 6 illustrates a functional block diagram of the external device 106 in accordance with one embodiment. The external device 106 may be utilized in a hospital setting, a physician's office, an EP lab, or even the patient's home to communicate with the IMD 102 (shown in FIG. 1) to receive cardiac signals from the IMD 102 and to receive cardiac parameters from one or more of the sensors 136, 138, 140, 142 (shown in FIG. 1). As described above, the external device 106 may receive the cardiac signals and cardiac parameters that are obtained during the induced VT event in real time, or during the induced VT event as the cardiac signals and cardiac parameters are obtained.

The external device 106 includes an internal bus 600 that connects/interfaces with the evaluation processor 108. The external device 106 may include one or more tangible and non-transitory computer readable storage media, such as a ROM 604, RAM 606, and/or a hard drive 608. The external device 106 may include one or more input and/or output devices, such as a speaker 610, a printer 612, a CD-ROM or DVD drive 614, a floppy or disk drive 616, a parallel I/O circuit 618, a serial I/O circuit 620, the display device 144, a touch screen 624, a standard keyboard connection 626, custom keys 628, a telemetry subsystem 630, and a wireless channel 666. The parallel and/or serial I/O circuits 618, 620 may be communicatively coupled with the sensors 136, 138, 140 (shown in FIG. 1) to receive cardiac parameters from the sensors 136, 138, 140. The evaluation processor 108 may include a microprocessor, a micro-controller, or equivalent control circuitry, designed to operate according to a set of instructions stored on a computer readable storage medium, such as one or more of the ROM 604, RAM 606, and/or hard drive 608.

The display device 144 (for example, may be connected to a video display 632) and/or the touch screen 624 may display text, alphanumeric information, data and graphic information via a series of menu choices to be selected by the user relating to the IMD 102 (shown in FIG. 1). By way of example only, the display device 144 may present a graphical display of the heart 104 (shown in FIG. 1) that includes graphical representations of VT rotors, conduction pathways, and other areas of the heart 104 that associated with the clinical and/or induced VT events. The display device 144 may present the graphical representations to guide a physician in performing an ablation procedure to the heart 104 during the induced VT event.

The touch screen 624 accepts a user's touch input 634 when selections are made. The keyboard 626 (for example, a typewriter keyboard 636) allows the user to enter data to the displayed fields, operational parameters, therapy parameters, as well as interface with the telemetry subsystem 630. Furthermore, custom keys 628 turn on/off 638 (for example, an emergency VVI key (EVVI) that sets the IMD 102 (shown in FIG. 1) to a safe VVI mode) the external device 106. The printer 612 prints hard-copies of reports 640 for a physician/healthcare worker to review or to be placed in a patient file, and speaker 610 provides an audible warning (for example, sounds and tones 642) to the user in the event a patient has any abnormal physiological condition occur while the external device 106 is being used. The parallel I/O circuit 618 interfaces with a parallel port 644. The serial I/O circuit 620 interfaces with a serial port 646. The sensors 136, 138, 140 (shown in FIG. 1) may be coupled with the parallel and/or serial ports 644, 646 to communicate cardiac parameters to the parallel and serial I/O circuits 618, 620. The drive 616 accepts disks or diskettes 648. The drive 614 accepts CD and/or DVD ROMs 650. The wireless channel 666 may be a connection capable of wirelessly communicating data with external devices. For example, the wireless channel 666 may send and/or receive wireless signals 668 over a Wi-Fi or Bluetooth channel or connection.

The telemetry subsystem 630 includes a processing unit 652 in electrical communication with a telemetry circuit 654, which communicates with both an ECG circuit 656 and an analog out circuit 658. The ECG circuit 656 is connected to ECG leads 660. The ECG leads 660 are joined with the ECG sensor 142 (shown in FIG. 1), such as electrodes joined to the outside of a patient's body, to obtain ECG signals. The telemetry circuit 654 is connected to a telemetry wand 662. The analog out circuit 658 includes communication circuits, such as a transmitting antenna, modulation and demodulation stages (not shown), as well as transmitting and receiving stages (not shown) to communicate with analog outputs 664. The external device 106 may wirelessly communicate with the IMD 102 (shown in FIG. 1) and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 106 to the IMD 102 (for example, an electrical cable having a USB connection).

Figure 7:
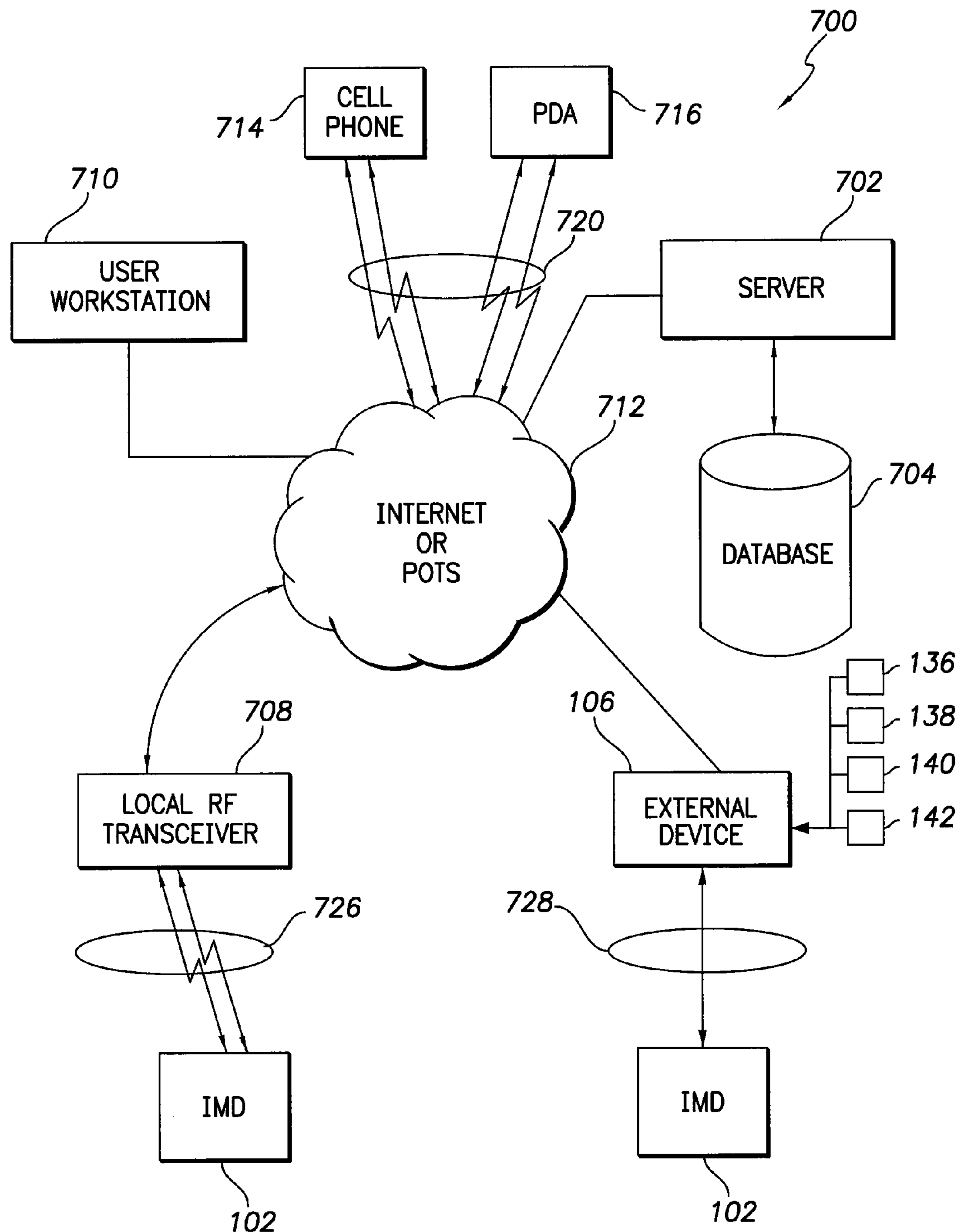
FIG. 7 illustrates a patient data network in accordance with one embodiment.

FIG. 7 illustrates a distributed patient data network 700 in accordance with one embodiment. The patient data network 700 includes the server 702 that is connected to the database 704, the external device 106, a local RF transceiver 708, and a user workstation 710 electrically connected to a communication system 712. The communication system 712 may be an internet, the Internet or a portion thereof, a voice over IP (VoIP) gateway, a local plain old telephone service (POTS), such as a public switched telephone network (PSTN), and the like. Alternatively, the communication system 712 may be a local area network (LAN), a campus area network (CAN), a metropolitan area network (MAN), or a wide area network (WAN). The communication system 712 serves to provide a network that facilitates the transfer of cardiac signals and parameters to enable the external device 106 and/or the IMD 102 to determine if a clinical VT event and an induced VT event are a common type of VT event.

The server 702 is a computer system that provides services to other computing systems (for example, clients) over a computer network. The server 702 acts to control the transmission and reception of information such as cardiac signals and cardiac parameters. The server 702 interfaces with the communication system 712, such as the internet, Internet, or a local POTS based telephone system, to transfer information between the external device 106, the local RF transceiver 708, the user workstation 710 (as well as other components and devices) to the database 704 for storage/retrieval of records of information. By way of example only, these other components and devices may include a cell phone 714 and/or a personal data assistant (PDA) 716. The server 702 may download cardiac signals and/or cardiac parameters, via a wireless connection 720, to the cell phone 714 or the PDA 716.

Database 704 is any commercially available database that stores information in a record format in electronic memory. The database 704 stores information such as cardiac signals and cardiac parameters that were obtained during and/or following a clinical VT event and/or an induced VT event. The information is downloaded into the database 704 via the server 702 or, alternatively, the information is uploaded to the server 702 from the database 704.

In one embodiment, the external device 106 receives cardiac parameters that were obtained by the sensors 136, 138, 140, 142 during and/or following a clinical VT event and cardiac signals that were obtained by the IMD 102 during and/or following the clinical VT event. The IMD 102 may communicate with the external device 106 by a wireless connection 728. During and/or following the induced VT event, the cardiac parameters and cardiac signals are communicated to the external device 106. The cardiac parameters may be directly communicated to the external device 106 from the sensors 136, 138, 140, 142 or may be communicated to the IMD 102, which then communicates the cardiac parameters to the external device 106. The external device 106 communicates the cardiac parameters and/or cardiac signals from the clinical VT event and the induced VT event to the server 702 by way of the communication system 712 for analysis and/or storage on the database 704 in one embodiment.

In order to compare the cardiac signals of an induced VT event with previously acquired cardiac signals of a clinical VT event, the external device 106 may obtain the cardiac signals of the clinical VT event from the database 704 and/or workstation 710 by way of the communication system 712. Similarly, in order to compare the cardiac parameters of the induced VT event with previously acquired cardiac parameters of the clinical VT event, the external device 106 may obtain the cardiac parameters of the clinical VT event from the database 704 and/or workstation 710 by way of the communication system 712. Alternatively, the external device 106 may communicate the cardiac parameters and/or cardiac signals from the clinical VT event and the induced VT event to the workstation 710 by way of the communication system 712 for analysis and/or storage. For example, the server 702 and/or user workstation 710 may compare the cardiac signals of the induced VT event with the cardiac signals of the clinical VT event to determine if the clinical and induced VT events are a common type of event. The server 702 and/or user workstation 710 may compare the cardiac parameters of the induced VT event with the cardiac parameters of the clinical VT event to determine if the clinical and induced VT events are the common type of event.

In one embodiment, the IMD 102 may communicate with the external device 106, workstation 710, and/or server 702 by way of a wireless connection 726 with the local RF transceiver 708. The local RF transceiver 708 interfaces with the communication system 712 to upload the cardiac signals acquired by the IMD 102 to the server 702 and/or workstation 710.

The user workstation 710 may interface with the communication system 712 to download data via the server 702 from the database 704. Alternatively, the user workstation 710 may download cardiac signals and/or cardiac parameters from the IMD 102 and/or external device 106. Once the user workstation 710 has downloaded the cardiac signals and/or cardiac parameters, the user workstation 710 may process the cardiac signals and/or parameters. For example, the user workstation 710 may be used to determine if an induced VT event is similar to a clinical VT event based on differences between the cardiac signals and/or differences between the cardiac parameters, as described above. Once the user workstation 710 has finished performing its calculations, the user workstation 710 may either download the results to the external device 106 and/or the database 704.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cardiac analysis system comprising:

an implantable medical device (IMD) including electrodes configured to be positioned proximate to a heart, the electrodes sensing cardiac signals of the heart including first cardiac signals associated with a clinical ventricular tachycardia (VT) event of the heart and second cardiac signals associated with an induced VT event of the heart;

at least one sensor configured to measure non-electrical cardiac parameters of the heart including first non-electrical cardiac parameters associated with the clinical VT event and second non-electrical cardiac parameters associated with the induced VT event and wherein the at least one sensor is selected from the group consisting of a blood pressure sensor, a blood oxygen sensor, a photoplethysmograph (PPG) sensor, a glucose sensor, an acoustic sensor, and a saturated venous oxygen sensor; and an external device configured to receive the first and second cardiac signals, the external device configured to receive the first and second non-electrical cardiac parameters, the external device configured to present the first cardiac signals and the first non-electrical cardiac parameters with the second cardiac signals and the second non-electrical cardiac parameters to enable determination of when the clinical VT event and the induced VT event are a common type of VT event.

2. The cardiac analysis system of claim 1, wherein the external device is configured to receive the first non-electrical cardiac parameters and the first cardiac signals prior to the induced VT event.

3. The cardiac analysis system of claim 1, wherein the external device is configured to receive the second non-electrical cardiac parameters and the second cardiac signals in real time during the induced VT event.

4. The cardiac analysis system of claim 1, wherein the external device is configured to receive the second non-electrical cardiac parameters and the second cardiac signals during an ablation procedure applied to the heart and to determine when the clinical VT event and the induced VT event are the common type of VT event during the ablation procedure.

5. The cardiac analysis system of claim 1, wherein the IMD is configured to apply stimulus pulses to the heart during a pacing regimen while the IMD obtains the first cardiac signals and the at least one sensor measures the first non-electrical cardiac parameters, the IMD further configured to apply the pacing regimen to the heart while the IMD obtains the second cardiac signals and the at least one sensor measures the second non-electrical cardiac parameters.

6. The cardiac analysis system of claim 1, wherein the first and second non-electrical cardiac parameters measured by the at least one sensor are uncorrelated to the first and second cardiac signals sensed by the IMD.

7. The cardiac analysis system of claim 1, wherein the IMD is configured to deliver stimulus pulses to the heart according to a pacing regimen during the induced VT event, the IMD configured to apply the pacing regimen to the heart during a post-ablation VT event based on a comparison between the second cardiac signals associated with the induced VT event, and third cardiac signals obtained during the post-ablation VT event.

8. A method for comparing ventricular tachycardia (VT) events of a heart, the method comprising:

sensing cardiac signals of the heart using electrodes positioned proximate to the heart, the cardiac signals including first cardiac signals associated with a clinical VT event and second cardiac signals associated with an induced VT event;

measuring non-electrical cardiac parameters representative of the heart using at least one sensor, the non-electrical cardiac parameters including first non-electrical cardiac parameters associated with the clinical VT event and second non-electrical cardiac parameters associated with the induced VT event and wherein the non-electrical cardiac parameters are selected from the group consisting of blood pressure, blood oxygen saturation, photoplethysmography, glucose level, acoustic level, and saturated venous oxygen; and comparing the first cardiac signals with the second cardiac signals and comparing the first non-electrical cardiac parameters with the second non-electrical cardiac parameters to determine when the clinical VT event and the induced VT event are a common type of VT event.

9. The method of claim 8, wherein the sensing includes sensing the first cardiac signals prior to sensing the second cardiac signals and the measuring includes measuring the first non-electrical cardiac parameters event prior to measuring the second non-electrical cardiac parameters.

10. The method of claim 8, further comprising communicating the second cardiac signals and the second non-electrical cardiac parameters to an external device for presentation on a display device during the induced VT event.

11. The method of claim 8, wherein the sensing includes sensing the second cardiac signals during an ablation procedure applied to the heart, the measuring includes measuring the second non-electrical cardiac parameters during the ablation procedure, and the comparing includes comparing, during the ablation procedure, the second cardiac signals with the first cardiac signals and comparing the second non-electrical cardiac parameters with the first non-electrical cardiac parameters.

12. The method of claim 8, further comprising applying stimulus pulses to the heart according to a pacing regimen during the clinical VT event, wherein the sensing the first cardiac signals associated with the clinical VT event and the measuring the first non-electrical cardiac parameters associated with the clinical VT event occurs during the pacing regimen.

13. The method of claim 8, further comprising applying stimulus pulses to the heart according to a pacing regimen during the induced VT event, wherein the sensing the second cardiac signals associated with the induced VT event and the measuring the second non-electrical cardiac parameters associated with the induced VT event occurs during the pacing regimen.

14. The method of claim 8, wherein the measuring the first and second non-electrical cardiac parameters includes measuring the first and second cardiac parameters that are uncorrelated to the first and second cardiac signals of the heart.

15. The method of claim 8, further comprising supplying stimulus pulses to the heart according to a pacing regimen during the induced VT event and applying the pacing regimen to the heart during a post-ablation VT event based on a comparison between the second cardiac signals associated with the induced VT event and third cardiac signals sensed during the post-ablation VT event.

16. A tangible and non-transitory computer readable storage medium for a cardiac analysis system comprising an implantable medical device (IMD) having electrodes positioned proximate to a heart, at least one sensor, and an evaluation processor, the computer readable storage medium including instructions to direct the evaluation processor to:

receive first cardiac signals sensed by the electrodes of the IMD and receive first non-electrical cardiac parameters measured by the at least one sensor and associated with a clinical ventricular tachycardia (VT) event, the first cardiac signals and the first non-electrical cardiac parameters representative of cardiac activity of the heart;

receive second cardiac signals sensed by the electrodes of the IMD and receive second non-electrical cardiac parameters measured by the at least one sensor and associated with an induced VT event; and determine when the clinical VT event and the induced VT event are a common type of VT event by comparing the first cardiac signals associated with the clinical VT event with the second cardiac signals associated with the induced VT event and comparing the first non-electrical cardiac parameters associated with the clinical VT event with the second non-electrical cardiac parameters associated with the induced VT event.

17. The computer readable storage medium of claim 16, wherein the instructions direct the evaluation processor to receive the first non-electrical cardiac parameters associated with the clinical VT event and receive the first cardiac signals associated with the clinical VT event prior to the induced VT event and to receive the second non-electrical cardiac parameters associated with the induced VT event and the second cardiac signals associated with the induced VT event during the induced VT event.

18. The computer readable storage medium of claim 16, wherein the instructions direct the evaluation processor to determine if the clinical VT event and the induced VT event are the common type of VT event by comparing indices of the first cardiac signals associated with the clinical VT event with indices of the second cardiac signals associated with the induced VT event, the indices including at least one of a VT cycle length, a variability of VT cycle lengths, a rate of ventricular contraction, a variability of ventricular contractions, an amplitude, a waveform morphology measurement, or a frequency index.

* * * * *